(12) United States Patent
Bender

(10) Patent No.: US 10,392,322 B2
(45) Date of Patent: Aug. 27, 2019

(54) PROCESS AND APPARATUS FOR RECOVERING AROMATIC HYDROCARBONS

(71) Applicant: ExxonMobil Chemical Patents Inc., Baytown, TX (US)

(72) Inventor: Timothy P. Bender, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 347 days.

(21) Appl. No.: 15/175,400

(22) Filed: Jun. 7, 2016

(65) Prior Publication Data

US 2017/0029348 A1 Feb. 2, 2017

Related U.S. Application Data

(60) Provisional application No. 62/198,777, filed on Jul. 30, 2015.

(51) Int. Cl.
| | | |
|---|---|---|
| C07C 7/00 | (2006.01) | |
| C07C 7/04 | (2006.01) | |
| C10G 65/06 | (2006.01) | |
| C10G 67/04 | (2006.01) | |
| B01D 3/14 | (2006.01) | |
| C07C 7/08 | (2006.01) | |
| B01D 3/40 | (2006.01) | |
| C10G 65/08 | (2006.01) | |
| C10G 7/08 | (2006.01) | |

(52) U.S. Cl.
CPC .............. *C07C 7/005* (2013.01); *B01D 3/141* (2013.01); *B01D 3/143* (2013.01); *B01D 3/40* (2013.01); *C07C 7/04* (2013.01); *C07C 7/08* (2013.01); *C10G 7/08* (2013.01); *C10G 65/06* (2013.01); *C10G 65/08* (2013.01); *C10G 67/04* (2013.01)

(58) Field of Classification Search
CPC .......... C10G 7/08; C10G 65/06; C10G 65/08; C10G 67/04; C07C 7/005; C07C 7/08; B01D 3/141; B01D 3/143; B01D 3/40
See application file for complete search history.

(56) References Cited

U.S. PATENT DOCUMENTS

| 8,680,358 B1 | 3/2014 | Lee et al. |
| 2012/0080288 A1* | 4/2012 | Petri .................. C10G 65/04 196/46 |

FOREIGN PATENT DOCUMENTS

| GB | 1 301 019 | * 12/1972 | ......... C10G 67/0427 |
| GB | 1301019 | 12/1972 | |

OTHER PUBLICATIONS

Mostoufi, Navid et al, "Simulation of an Industrial Pyrolysis Gasoline Hydrogenation Unit", Chem. Eng. Technol., 2005, 28, No. 2.*

* cited by examiner

*Primary Examiner* — Renee Robinson

(57) ABSTRACT

The present invention relates to an improved extractive distillation process for recovering aromatic hydrocarbons from non-aromatic hydrocarbons in naphtha streams containing heavy hydrocarbon contaminants wherein each contaminant is characterized as having a boiling point in the range of between that of the separated non-aromatic hydrocarbons and the extractive distillation solvent utilized to recover and purify the aromatic hydrocarbons.

13 Claims, 4 Drawing Sheets

PROCESS AND APPARATUS FOR RECOVERING AROMATIC HYDROCARBONS

PRIORITY

This invention claims priority to and the benefit of U.S. Ser. No. 62/198,777 filed on Jul. 30, 2015, which is incorporated herein by reference.

FIELD OF THE INVENTION

The invention relates to a process for recovering aromatic hydrocarbons, specifically benzene, toluene, and xylenes, from a naphtha stream using an extractive distillation process for the separation of aromatics from non-aromatics.

BACKGROUND OF THE INVENTION

Aromatic hydrocarbons, such as benzene, toluene and xylenes (collectively, "BTX"), serve as important building blocks for a variety of plastics, foams and fibers. Often these compounds are produced via catalytic reformation of naphtha through steam cracking of naphtha or gas oils, or other methods where substantial amounts of non-aromatic compounds are present.

The useful aromatic hydrocarbons may be separated from the non-aromatic hydrocarbons by, for example, solvent extraction. One widely used solvent extraction technique that is well known to those of ordinary skill in the art is the sulfolane process developed by UOP and Shell Oil Co. The process uses tetrahydrothiophene-1,1-dioxide (or sulfolane) as a solvent and water as a co-solvent to preferentially extract the desired BTX compounds from non-aromatic hydrocarbons. However, as is well known, other solvents having similar properties may also be used (e.g., glycols, N-FormylMorpholine (NFM) and N-Methyl-2-pyrrolidone (NMP)).

One embodiment of the sulfolane process uses extractive distillation, wherein a hydrocarbon feed containing aromatic and non-aromatic compounds is fed to a multistage distillation tower in which a circulating solvent (e.g., sulfolane) is present. The solvent changes the relative volatility of the aromatic/non-aromatic compounds such that aromatic compounds can be separated from the non-aromatic compounds. The non-aromatic compounds are fractionated overhead, while the aromatic compounds exit out the bottom of the tower along with the higher boiling solvent. The aromatic compounds are then separated from the solvent in another multistage column, such that the majority of the desired aromatic compounds are fractionated overhead while the majority of the solvent is recovered out the bottom of the tower. The solvent is then recycled back to the extractive distillation tower.

The presence of any heavy feed compounds (either aromatic or non-aromatic) entering the extractive distillation process through the fresh solvent, or any other stream that may be fed to the extractive distillation unit, poses a particular problem in that there is no escape avenue for these compounds in either the non-aromatic or aromatic fractions. As such, these heavy compounds, which distill in a similar range (co-boil) with the solvent, will accumulate in the solvent phase, which is detrimental to the performance of the process. An accumulation of heavy compounds in the solvent can cause an increase in the energy needed for separation of the aromatic and non-aromatic compounds, a decrease in unit capacity, a decrease in unit reliability, or a combination thereof. It is therefore desirable to remove these heavy compounds.

Traditionally, a regeneration (purification) process for an extractive distillation solvent is designed to remove very heavy byproduct compounds, such as thermal or oxidative degradation products of the solvent, as disclosed in U.S. Pat. No. 5,053,137. However, the present inventors have found that certain heavy feed compounds co-boil closely to the solvent under solvent regeneration conditions, and therefore, cannot be effectively removed using this process. Solutions proposed in the prior art include the use of adsorption beds, as disclosed in U.S. Pat. No. 8,552,247, or the use of a raffinate wash, as disclosed in U.S. Patent Application Publication No. 2010-0300939. Other techniques involve processing the extractive distillation solvent through a liquid-liquid extraction unit that is more effective at rejecting the heavy compounds, as disclosed by U.S. Pat. No. 8,860,358 and PCT Publication No. WO 2014/209585.

However, efficient and effective removal of the detrimental heavy compounds from the feedstocks prior to the extractive distillation process would eliminate the need for costly and energy intensive additional steps to purify the extractive distillation solvent.

SUMMARY OF THE INVENTION

This invention provides an improved process and apparatus for recovering aromatic hydrocarbons, such as benzene, toluene and/or xylenes, from non-aromatic hydrocarbons in naphtha streams containing heavy hydrocarbon contaminants via extractive distillation. More specifically, a process for providing an improved feedstock for an extractive distillation process is provided. Removing the heavy hydrocarbon contaminants from the feed stream prior to the extractive distillation unit prevents undesirable buildup of such heavy compounds in the extractive distillation unit and eliminates the need for costly additional steps to purify the extractive distillation solvent. Apparatuses for such methods are also provided.

In one embodiment, a naphtha stream comprising aromatic and non-aromatic hydrocarbons is provided to a first stage hydrofiner to remove dienes and styrenes and produce a first stage hydrofiner effluent stream. The first stage hydrofiner effluent stream is passed to a divided wall column from which a $C_{6+}$ hydrocarbon stream is recovered. The $C_{6+}$ hydrocarbon stream is processed through a second stage hydrofiner to produce a second stage hydrofiner effluent stream, which is recycled back to the divided wall column. A twice hydrofined $C_{6+}$ hydrocarbon stream is then recovered from the divided wall column and passed to an extractive distillation unit to recover a product comprising benzene, toluene and/or xylenes. Using a divided wall column allows for more energy efficient operations and can reduce the equipment required for such an operation by at least three separation columns.

An apparatus for the above process is also provided. The apparatus comprises a first stage hydrofiner to produce a first stage hydrofiner effluent stream. The apparatus also comprises a divided wall column fluidly connected to the first stage hydrofiner to produce at least a $C_{6+}$ hydrocarbon stream and a twice hydrofined $C_{6+}$ hydrocarbon stream. A second stage hydrofiner is fluidly connected to the divided wall column so as to receive the $C_{6+}$ hydrocarbon stream and produce a second stage hydrofiner effluent that is recycled to the divided wall column, and an extractive distillation unit is fluidly connected to the divided wall column so as to receive the twice hydrofined $C_{6+}$ hydrocarbon stream and produce an aromatics product stream.

In another embodiment, a naphtha stream that has been twice hydrofined is passed through a second stage hydrofiner column to separate the stream into a $C_{6-}$ rich vapor overhead fraction and a $C_{10+}$ rich liquid bottoms fraction. A vapor side-stream comprising $C_6$-$C_{10+}$ hydrocarbons is removed from adjacent the bottom of the second stage hydrofiner column and passed through a rectification section to separate the vapor side stream into a stream rich in $C_{9+}$ hydrocarbons and a stream rich in $C_{6-8}$ hydrocarbons. The stream rich in $C_{6-8}$ hydrocarbons is then passed to an extractive distillation unit to recover a product comprising (i) benzene and/or toluene and (ii) xylene. The rectification section may be internal to or separate and external to the second stage hydrofiner column.

An apparatus for the above process is also provided. The apparatus comprises a second stage hydrofiner to produce a second stage hydrofiner effluent stream, and a fractionation column fluidly connected to the second stage hydrofiner to separate the second stage hydrofiner effluent stream into a $C_{6-}$ rich vapor overhead fraction, a $C_{10+}$ rich liquid bottoms fraction, and a vapor side-stream comprises $C_6$-$C_{10+}$ hydrocarbons. The apparatus also comprises a rectification section fluidly connected to the second stage hydrofiner column so as to receive the vapor side-stream and separate the vapor side-stream into a stream rich in $C_{9+}$ hydrocarbons and a stream rich in $C_{6-8}$ hydrocarbons. An extractive distillation unit is fluidly connected to the rectification section so as to receive the stream rich in $C_{6-8}$ hydrocarbons and produce an aromatics product stream.

These and other objects, features, and advantages will become apparent as reference is made to the following detailed description, preferred embodiments, examples, and appended claims.

DETAILED DESCRIPTION

This invention provides an improved extractive distillation process, and more specifically a process for providing an improved feedstock for an extractive distillation process, for recovering aromatic hydrocarbons from non-aromatic hydrocarbons in naphtha streams containing heavy hydrocarbon contaminants. For purposes of the present description and the appended claims, the term "heavy contaminant" refers to any hydrocarbon (e.g., aromatic) having a boiling point between that of the separated non-aromatics and the extractive distillation solvent and "boiling point" may refer to the normal boiling point or the effective boiling point. Typically, heavy contaminants comprise $C_{9+}$ aromatic hydrocarbons. In one of its specific applications, this invention relates to an improved extractive-distillation process for recovering aromatic hydrocarbons including benzene, toluene, and xylenes (BTX aromatics) from $C_6$-$C_8$ petroleum streams.

Figure 1A:
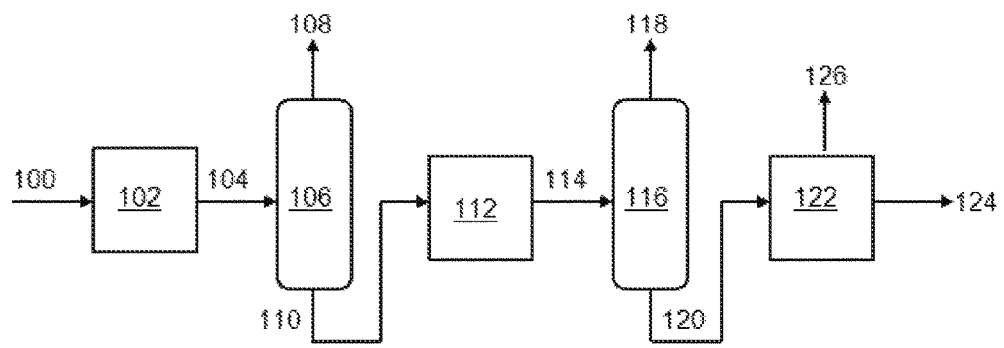
FIG. 1A is a schematic diagram of a conventional process for recovering aromatic hydrocarbons from a naphtha feed.

With reference to FIG. 1A, illustrating a conventional process, a naphtha stream 100 is processed through a first stage hydrofiner 102. As used herein, naphtha includes pygas, cat naptha, coker naphtha, hydrocracker naphtha, stream cracked naphtha and reformate. Pygas as used herein means a $C_6$-$C_{10+}$ cut of the pyrolysis effluent from a steam cracking furnace. Typically, the pyrolysis gasoline contains from about 15 to about 65 wt % benzene, and from about 5 to about 35 wt % toluene, and contains at least 1 wt % non-aromatics but can be up to 50 wt % non-aromatics depending on composition of feedstock to the steam cracker, intensity of the pyrolysis reaction, and separation and processing scheme for the pygas stream. Generally, as the intensity of the pyrolysis reaction increases, which can be noted by the rising outlet temperature of the reactor or by the changing of the ratio of two products, such as propylene and methane, more aromatics will be present in the effluent.

Other naphtha sources are cat naphtha, which is produced from a fluid catalytic cracker, and reformate, which is a common feedstock to traditional aromatics plants. Reformate is produced by contact of petroleum naphtha with a hydrogenation/dehydrogenation catalyst on a support and typically contains $C_5$ to $C_{12}$ hydrocarbons of which at least about 40 wt % comprises aromatics and at least about 1 wt % comprises non-aromatics but can be up to 50 wt % non-aromatics depending on composition of feedstock to the reformer and severity of the reforming reaction.

The first stage hydrofiner 102 removes dienes and styrenes from the naphtha stream 100 via saturation with hydrogen (not shown) and the resulting first stage hydrofiner effluent stream 104 is separated in separation section 106. A $C_{5-}$ stream 108 recovered from the separation section 106 may be further processed by methods per se know in the art and a $C_{6+}$ aromatic hydrocarbon-containing stream 110 recovered from the separation section 106 is sent to a second stage hydrofiner 112 to reduce the olefins in the stream by selective hydrogenation of the olefins. Conventionally, the second stage hydrofiner effluent stream 114 is fractionated in fractionation column 116 to provide a $C_{6-}$ overheads stream 118 and $C_{6+}$ bottoms stream 120, which is sent to extractive distillation 122 to separate the aromatic compounds 124 from the non-aromatic compounds 126. However, in the second stage hydrofiner 112 there are some unwanted side reactions in which olefins alkylate aromatics rather than saturating with hydrogen, forming $C_{12+}$ by-products, and as explained above in the background, the presence of these heavy compounds has a detrimental effect on the extractive distillation process.

To avoid the buildup of heavy compounds in the extractive distillation solvent, the separation of the very heavy aromatic components can be performed prior to sending the hydrocarbon stream to extractive distillation for the recovery of the aromatic hydrocarbons.

One known method of adjusting the composition of the $C_{6+}$ fraction sent to extractive distillation is to separate the second stage hydrofiner effluent stream 114 in second stage hydrofiner column 116 into a $C_{6-}$ overheads stream and a $C_{10+}$ bottoms stream. A liquid side stream comprising $C_6$-$C_{10+}$ hydrocarbons is removed from adjacent to the bottom of the tower and used as the extractive distillation feed. Although this option minimizes capital investment and energy cost, it only partially removes the deleterious heavy components in the feed since the feed enters the column above where the side stream is removed, and so does not eliminate the issue of heavy components building up in the extractive distillation solvent.

Another known method of adjusting the composition of the $C_{6+}$ fraction sent to extractive distillation is to again separate the second stage hydrofiner effluent stream 114 in second stage hydrofiner column 116 into a $C_{6-}$ overheads stream and a $C_{10+}$ bottoms stream. In this case, however, the $C_{10+}$ bottoms stream is vaporized and fed to in a separate heavy aromatics tailing column, where it is separated into a $C_6$-$C_8$ overhead stream, which is used as the feed to the extractive distillation process, and a $C_{9+}$ bottoms stream. A heating means (not shown) for the $C_{10+}$ bottoms stream is advantageous but optional as column 116 is generally operated at a higher pressure than the heavy aromatics tailing column. While the heavy aromatics tailing column is effective in removing most of the deleterious heavy components in the feed, it requires significant capital and energy expenditure.

Figure 2B:
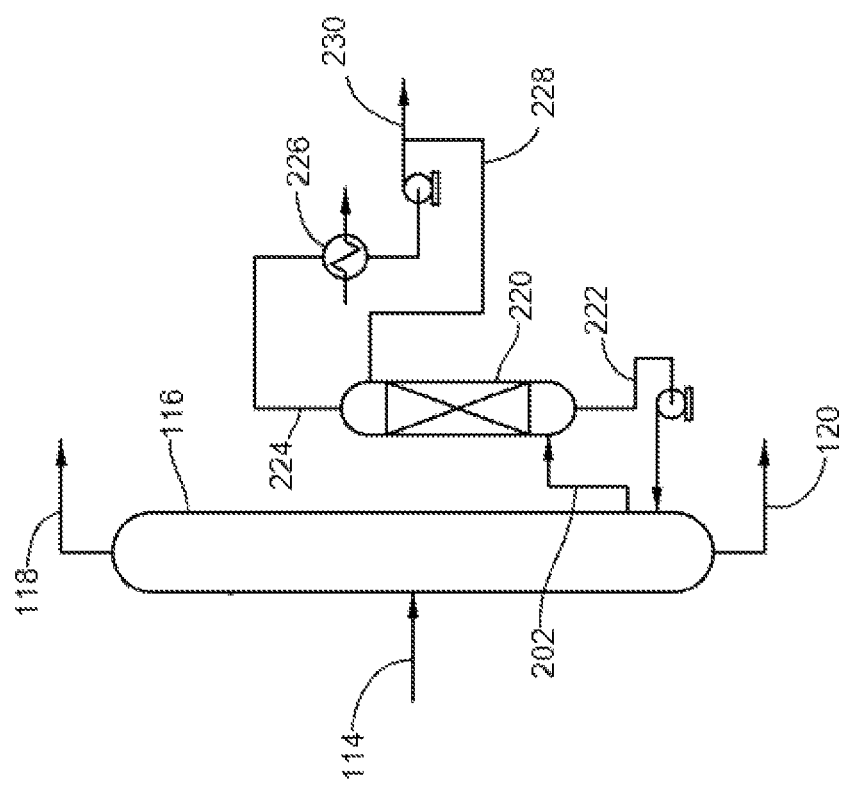
FIG. 2B is a schematic diagram showing a portion of an apparatus for separating $C_{6-8}$ hydrocarbons from a naphtha feed according to a second embodiment of the present invention.
Figure 2A:
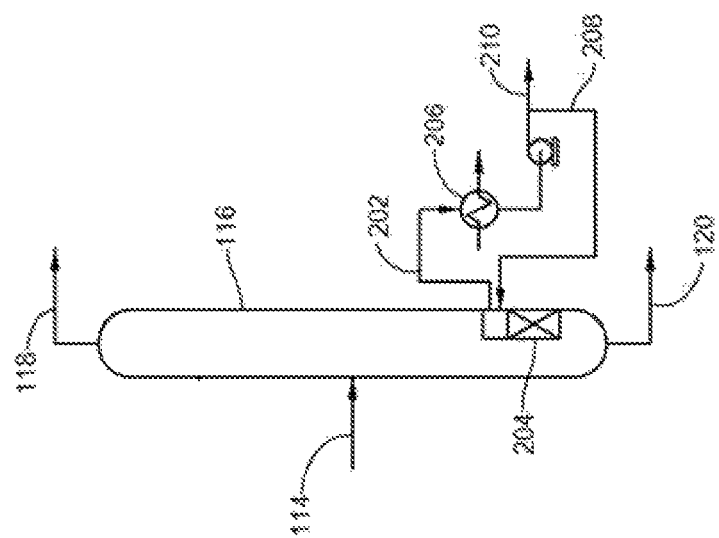
FIG. 2A is a schematic diagram showing a portion of an apparatus for separating $C_{6-8}$ hydrocarbons from a naphtha feed according to an embodiment of the invention.

A first example of the present improved treatment process is shown in FIG. 2A, in which the second stage hydrofiner effluent stream 114 is fed to fractionation column 116, where the feed is fractionated into $C_{6-}$ overheads stream 118 and a $C_{10+}$ bottoms stream 120. In addition, a vapor side-stream 202 is removed from an internal $C_{6+}$ aromatics rectification section 204 of the fractionation column 116 adjacent the base of the column 116. The vapor side-stream 202 is then passed through a condenser 206, advantageously assisted by pump(s) shown symbolically and unnumbered in the figure, to condense a liquid stream 208 rich in $C_{9+}$ hydrocarbons which is typically recycled as reflux to the rectifier section 204, and leave a vapor stream 210 rich in $C_6$-$C_8$ hydrocarbons, which is used as the feed to the extractive distillation process.

A second example of the present improved treatment process is shown in FIG. 2B, in which the second stage hydrofiner effluent stream 114 is again fed to fractionation column 116, where the feed is fractionated into $C_{6-}$ overheads stream 118 and a $C_{10+}$ bottoms stream 120. A vapor side-stream 202 is again removed from the fractionation column 116 adjacent the base of the column 116, but in this case the side-stream 202 is fed to a $C_{6+}$ aromatics rectification section 220 separate from and external to the fractionation column 116. In embodiments, the rectification section 220 employs a smaller distillation column than the tailing column described above and does not have an external reboiler and therefore has lower capital and operating cost than the embodiment involving a separate heavy aromatics tailing column. The side-stream 202 is fractioned in the rectification section 220 into a liquid bottoms stream 222, which is returned to the column 116, and an overhead 224, which is passed through a condenser 226. Similar to FIG. 2A, the condenser 226 in FIG. 2B condenses a liquid stream 228 rich in $C_{9+}$ hydrocarbons from the overhead 224 (assisted by pump illustrated symbolically and unnumbered in the figure), which is typically recycled as reflux to the rectification section 220, and leave a vapor stream 230 rich in $C_6$-$C_8$ hydrocarbons, which is used as the feed to the extractive distillation process.

Figure 1B:
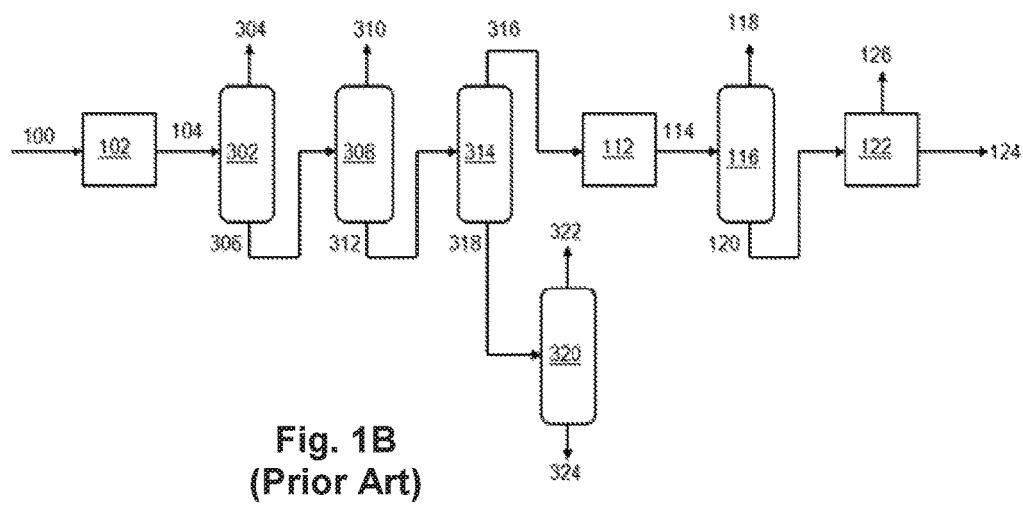
FIG. 1B is a schematic diagram of an alternate conventional process for recovering aromatic hydrocarbons from a naphtha feed.

In another, more preferred embodiment of the present improved treatment process, a divided wall column is used to consolidate the separation section 106 and fractionation column 116. In practice, separation section 106 may consist of multiple separation steps and columns and can be configured in a plurality of ways. For example, in one possible configuration of a conventional separation section shown in FIG. 1B, the separation section 106 comprises a separator, depentanizer, debenzenizer and rerun column. The first stage hydrofiner effluent stream 104 is passed through a separator 302 to remove a hydrogen and light gas stream 304 and $C_{5+}$ hydrocarbon-containing stream 306 is sent to a depentanizer column 308. The depentanizer column 308 provides a $C_{5-}$ hydrocarbon-containing stream 310 overhead and a $C_{6+}$ hydrocarbon-containing stream 312, which is sent to a debenzenizer column 314. The debenzenizer column 314 provides $C_{6-}$ hydrocarbon-containing stream 316 overhead and a $C_{7+}$ hydrocarbon-containing stream 318, which passes to a rerun column 320 to provide a debenzenized steam-cracked naphtha product stream 322 comprising toluene, ethylbenzene and $C_9$ aromatic hydrocarbons, which is sent to the mogas pool, and a stream-cracked gas oil stream 324, typically in the $C_{9+}$ range, which is sent to the refinery for recovery and or sometimes used as a fuel oil cutter stock. The $C_{6-}$ hydrocarbon-containing stream 316 is provided to the second stage hydrofiner 112, and the second stage hydrofiner effluent stream 114 is processed through fractionation column 116, which provides a $C_{6-}$ hydrocarbon-containing overheads stream 118 and a twice hydrofined $C_{6+}$ hydrocarbon stream 120 which is sent to extractive distillation 122. The rerun column 320 could alternatively be positioned after the second stage hydrofiner 112.

Figure 3:
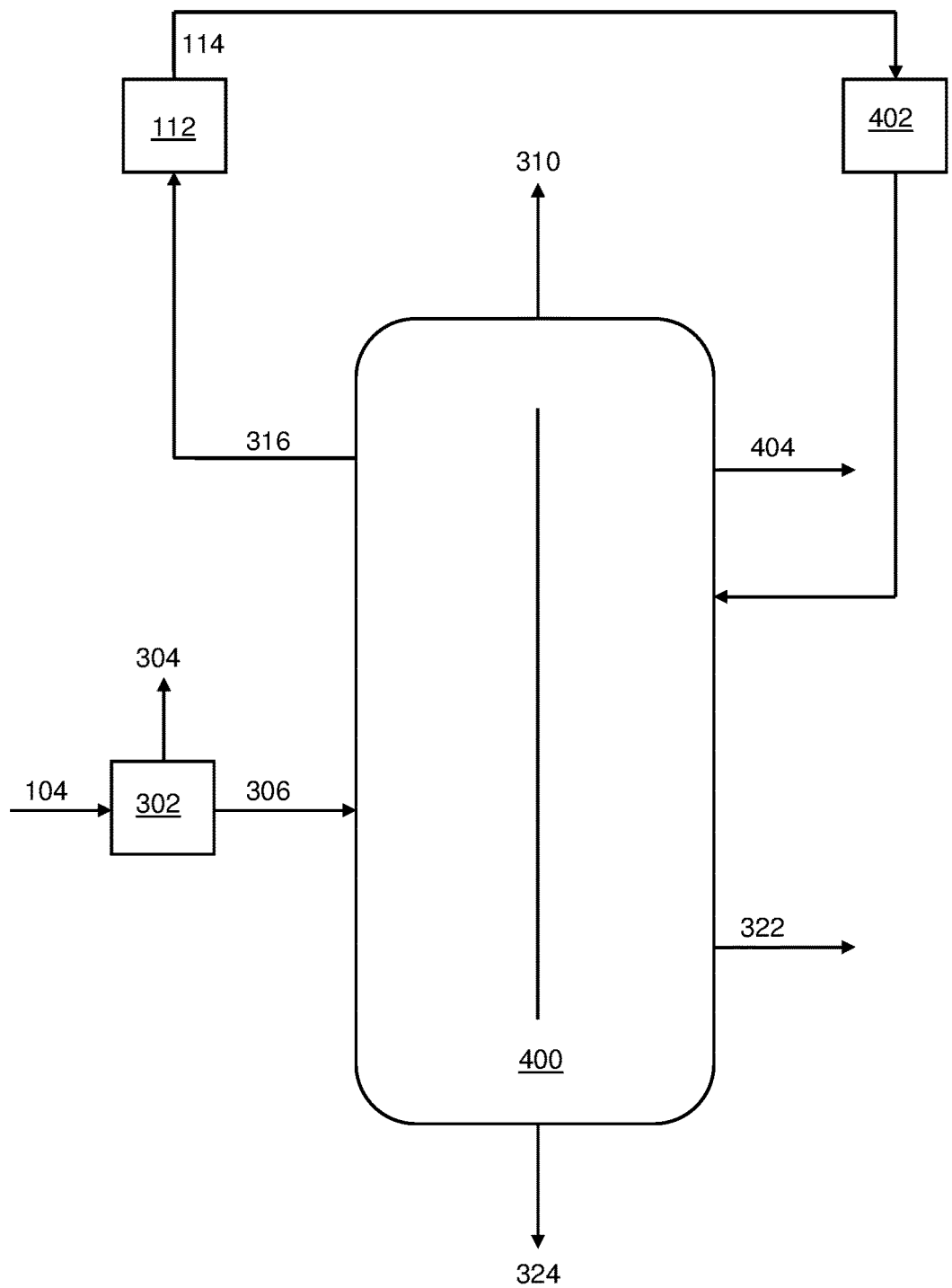
FIG. 3 is a schematic diagram showing a portion of an apparatus for separating $C_{6-8}$ hydrocarbons from a naphtha feed according to a third embodiment of the present invention.

FIG. 3 shows an embodiment of the present invention in which a divided wall column 400 is used for the many of the separations described in the FIG. 1A example. In this embodiment, the first stage hydrofiner effluent stream 104 passes through a first stage separator 302 to remove a hydrogen and light gas stream 304 and a $C_{5+}$ hydrocarbon-containing stream 306 is sent to the divided wall column 400. The divided wall column 400 produces a light gas stream 310 comprising $C_{5-}$ hydrocarbons withdrawn from the upper portion of the column, a debenzenized steam-cracked naphtha product stream 322, withdrawn from the lower portion of the column on the opposite side of the dividing wall than the first stage hydrofiner effluent stream 104 is introduced and which is sent to the mogas pool, and a stream-cracked gas oil stream 324 withdrawn from the bottom portion of the column, which is sent to the refinery.

A $C_{6+}$ hydrocarbon (benzene heart cut) stream 316 is recovered from the upper portion of the divided wall column 400 on the same side of the dividing wall as the first stage hydrofiner effluent stream 104 input location. The $C_{6+}$ hydrocarbon stream 316 is sent to the second stage hydrofiner 112, and the second stage hydrofiner effluent stream 114 is recycled back, through a second stage separator 402 to remove hydrogen and light gases, to the divided wall column 400 on the opposite side of the dividing wall from where the $C_{6+}$ hydrocarbon stream 316 is withdrawn. The first stage separator 302 and second stage separator 402 may be separate, independent equipment or combined into a single separator. A twice hydrofined $C_{6+}$ hydrocarbon stream 404 is removed from the upper portion of the divided wall column 400 on the same side of the dividing wall as the second stage hydrofiner effluent stream 114 is introduced and is sent to extractive distillation 122. One skilled in the art can determine the appropriate locations for the input and withdrawal of the above streams based upon their skill and the above disclosure of approximate locations. Using a divided wall column to perform substantially the same separations as separation section 106 and fractionator 116 reduces the equipment by at least three less separation columns and is more energy efficient.

Figure 4:
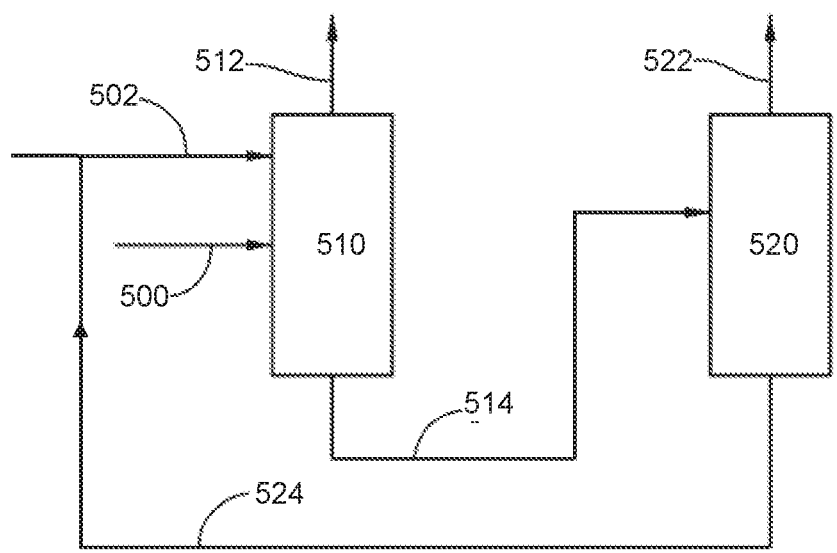
FIG. 4 is a schematic of an extractive distillation process.

Referring now to FIG. 4, the $C_6$-$C_8$ hydrocarbon stream, vapor stream 210 in FIG. 2A, vapor stream 230 in FIG. 2B, or twice hydrofined benzene heart cut stream 404 in FIG. 3, collectively referenced by 500 in FIG. 4, is introduced into a middle portion of extractive distillation column 510 and a solvent-rich stream 502 is fed into an upper portion of the column. The solvent may be sulfolane, NFM NFormylmorpholin, N-Methyl-2-pyrrolidone (NMP), or any other suitable solvent known in the art. A non-aromatic hydrocarbon rich stream 512 is recovered from the upper portion of the extractive-distillation column. A solvent-rich stream 514 containing the solvent, aromatic hydrocarbons, and heavy contaminant is recovered from a bottom portion of the extractive distillation column and is fed into a middle portion of solvent-recovery fractionating column 520. An aromatic-rich stream 522 comprising benzene, toluene and/or xylenes is recovered from an upper portion of the solvent-recovery fractionating column. A solvent-rich stream 524 containing solvent and any heavy contaminants remaining introduced in the feed is removed from a bottom portion of the solvent-recovery column and recycled into the extractive distillation column with the solvent-rich stream 502.

Any one of the above described inventive embodiments provide efficient and effective removal of the detrimental heavy compounds from the naphtha feedstocks prior to the extractive distillation process and can eliminate, or at least minimize, the need for costly additional steps to purify the extractive distillation solvent. Additionally, the described embodiments could be modified to apply to any selective hydrogenation process scheme in which olefinic species, such as di-olefins or cyclo-olefins, are selectively hydrogenated but undesired side reactions also occur to produce heavy byproducts. A specific example of a selective hydrogenation scheme in which this technology could be adapted is the selective hydrogenation of styrene, as disclosed in U.S. Patent Publication No. 2014/0221710, in a process to produce paraxylene from methanol, such as toluene methylation or methanol to aromatics.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. All numerical ranges are inclusive of the upper and lower numerical limits. While the illustrative embodiments of the invention have been described with particularity, it will be understood that various other modifications will be apparent to and can be readily made by those skilled in the art without departing from the spirit and scope of the invention.

What is claimed is:

1. A process for recovering aromatic hydrocarbons comprising benzene, toluene, and/or xylenes from a naphtha stream comprising aromatic and non-aromatic hydrocarbons, the process comprising:
   (a) providing a naphtha stream comprising aromatic and non-aromatic hydrocarbons and $C_{9+}$ hydrocarbons to a first stage hydrofiner to remove dienes and styrenes and to produce a first stage hydrofiner effluent stream;
   (b) passing said first stage hydrofiner effluent stream to a divided wall column to recover a $C_{6+}$ hydrocarbon stream, wherein the divided-wall column has a dividing wall that allows liquid to pass through in the bottom portion thereof;
   (c) passing said $C_{6+}$ hydrocarbon stream through a second stage hydrofiner to produce a second stage hydrofiner effluent stream;
   (d) recycling said second stage hydrofiner effluent stream back to said divided wall column;
   (e) recovering a twice hydrofined $C_{6+}$ hydrocarbon stream from a side location above the bottom portion of said divided wall column;
   (f) passing said twice hydrofined $C_{6+}$ hydrocarbon stream to an extractive distillation unit to recover a product comprising benzene, toluene and/or xylenes; and
   (g) obtaining a gas oil stream from the bottom portion of the divided wall column.

2. The process of claim 1, wherein said first stage hydrofiner effluent stream is passed through a first stage separator prior to step (b) to remove hydrogen and light gases.

3. The process of claim 1, wherein said second stage hydrofiner effluent stream is passed through a second stage separator prior to step (d) to remove hydrogen and light gases.

4. The process of claim 1, wherein step (b) further comprises recovering a light gas stream comprising $C_{5-}$ hydrocarbons, and a debenzenized naphtha stream.

5. The process of claim 4, wherein said light gas stream comprising $C_{5-}$ hydrocarbons is withdrawn from an upper portion of said divided wall column, and said debenzenized naphtha stream is withdrawn in a lower portion of the column on the opposite side of said dividing wall than an input location of said first stage hydrofiner effluent.

6. The process of claim 1, wherein said $C_{6+}$ hydrocarbon stream is recovered from an upper portion of the divided wall column on the same side of the dividing wall as an input location of said first stage hydrofiner effluent stream.

7. The process of claim 1, wherein said second stage hydrofiner effluent stream is recycled back to said divided wall column at a location in a middle portion of said divided wall column below and on the opposite side of the dividing wall than a withdrawal location of said $C_{6+}$ hydrocarbon stream.

8. The process of claim 1, wherein said twice hydrofined $C_{6+}$ hydrocarbon stream is recovered from a location in the upper portion of the divided wall column above and on the same side of the dividing wall as the input location of said second stage hydrofiner effluent stream.

9. The process of claim 1, wherein said naphtha stream is selected from the group consisting of pygas, cat naptha, coker naphtha, hydrocracker naphtha, steam cracked naphtha and reformate.

10. The process of claim 1, wherein said extractive distillation unit uses a solvent selected from the group consisting of sulfolane, N-FormylMorpholine (NFM) and N-Methyl-2-pyrrolidone (NMP).

11. The process of claim 1, wherein the second stage hydrofiner effluent stream comprises C12+ hydrocarbons.

12. The process of claim 1, wherein the gas oil stream comprises C12+ hydrocarbons.

13. The process of claim 11, wherein the gas oil stream comprises C12+ hydrocarbons.

* * * * *